US00PP12412P2

(12) United States Plant Patent

Elsner

(10) Patent No.: US PP12,412 P2
(45) Date of Patent: Feb. 19, 2002

(54) VARIETY OF GERANIUM PLANT NAMED 'PACPAL'

(75) Inventor: Wilhelm Elsner, Dresden (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 09/636,380

(22) Filed: Aug. 11, 2000

(51) Int. Cl.[7] ..... A01H 5/00

(52) U.S. Cl. ..... Plt./325

(58) Field of Search ..... Plt./325

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct zonal geranium plant with bright pink colored flowers having some streaking above medium green foliage. The new cultivar has a more controlled growth habit and brighter colored flowers than 'Pink Expectations'.

1 Drawing Sheet

BACKGROUND OF THE INVENTION

The present invention comprises a new and distinct cultivar of *Pelargonium×hortorum* known by the varietal name 'PACPAL' (Oglevee No. 5254, Breeder No. P-3364). The new variety was discovered in a selected breeding program in Dresden, Germany. The new variety was first asexually reproduced by cuttings at Olglevee, Ltd. in Connellsville, Pa. The new variety has been trial and field tested at Connellsville and has been found to retain its distinctive characteristics through successive propagations.

The cultivar, when grown in a glass greenhouse in Connellsville, Pa. using natural light and temperatures of 60° F. night and 68° F. day, has a response time of six weeks from a rooted cutting to flowering in a 4 inch pot. The response time was determined on plants grown in soilless media employing constant fertilizer 200–250 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. The color readings were taken indoors under 200–220 foot candles of fluorescent cool white light. Color references are primarily to The R.H.S. Colour Chart of The Royal Horticultural Society of London.

PLANT

Classification:
- *Botanical.*—*Pelargonium×hortorum.*
- *Commercial.*—Pink EX II.

Form: Medium mound.
Height: 19–22 cm from media surface.
Spread: 40 cm in diameter.
Growth: Upright, free basal branching.
Strength: Does not require artificial support.

Foliage: Stalked leaf attachment; slightly reflective.
Rooting time: 14–21 days.
Leaves:
- *Size.*—Length: 6.5–9.0 cm. Width: 7.5–10.0 cm at widest point.
- *Shape.*—Reniform; cordate base.
- *Margin.*—Crenate.
- *Texture.*—Pubescent.
- *Color.*—Upper surface: Green Group 137C with zone of Yellow-Green Group 147A. Lower surface: Green Group 138B.
- *Ribs and veins.*—Venation: Palmate. Color: Yellow-Green Group 147C.

Petioles:
- *Color.*—Yellow-Green Group 146C.
- *Length.*—5.0–7.0 cm.
- *Diameter.*—2–3 mm.

Stem:
- *Color.*—Yellow-Green Group 146C with some shading of Greyed-Orange Group 175B.
- *Internode length.*—2.5–3.5 cm.
- *Diameter.*—0.7–0.9 cm.

THE BUD

Shape:
- *Overall.*—Elliptical cluster when just showing color.
- *Individual bud.*—Elliptical when just showing color.

Size:
- *Overall.*—3.8–4.2 cm in diameter.
- *Individual bud.*—1.2–1.4 long; 0.6–0.8 cm in diameter.

Number of buds per cluster: 17–28.
Color:
- *Sepals.*—Green group 138B.
- *Petals.*—Red group 38A.

INFLORESCENCE

Blooming habit: Continuous; free and early flowering.
- *Size.*—9.5–11.0 cm.

Borne: Floret on pedicel; pedicel on peduncle; 8.0–15.0 cm above foliage.
Florets:
- *Form.*—Slightly cupped; petals overlap; numerous petaloids add to the varied and interesting appearance.

*Number of florets per umbel.*—17–26.

*Size.*—Diameter: 4.0–4.5 cm. Depth: 1.8–2.0 cm.

*Petals.*—Color: Upper Surface: Outer-top edge of petals is Red Group 56 A. Depending on the petal, there are varying amounts of faint streaks of Red Group 52C; on some petals this streaking is barely visible and the outer-top edge of the petal appears to be solely Red Group 56A. On other petals the streaks are so significant as to lend a bright pink color to the outer-top area creating a much more significant appearance of the Red Group 52C. Color deepens toward the center of the petal; the color is much more vibrant of Red Group 41C and on some petals Red Group 44D. At times irregular streaking of Red Group 42C and Red Group 43C and Red Group 36D is present. Base of the petals is Red Group 36D. Lower surface: Colors vary significantly; outer edges of some petals are Red Group 56D while others have a darker color of Red Group 56A. The center of the petals are also irregular, varying greatly due to the color of the top of the petal; color range from at lightest Red Group 37D to Red Group 38A and Red Group 43D at darkest. Shape: Obovate. Size: 2.0–2.5 cm long; 1.5–2.0 cm across. Margin: Entire. Number per floret: 5–8.

*Texture and appearance.*—Smooth, velvety, reflective.

*Tonality from a distance.*—Flowers of striking coral-pink centers with edges of soft pink above distinctly zoned medium green foliage. The varying degrees of corals, pinks, and peaches with the wide array of irregular petaloids lends a dramatic effect to these flowers.

Petaloids:

*Quantity.*—0–6.

*Shape.*—Irregular; twisted, petal-like with cut edges, tubular.

*Color.*—Same as petals — including variety and intensity of colors.

Pedicel:

*Length.*—2.3–3.0 cm.

*Diameter.*—1.5–2.0 mm.

*Color.*—Yellow-Green Group 145A with some areas of Greyed-Orange Group 175B.

Peduncle:

*Length.*—13.0–16.0 cm.

*Diameter.*—0.3–0.4 cm.

*Color.*—Yellow-Green Group 144A with some faint areas of Greyed-Orange Group 175B.

Disease/pest resistance: No unusual susceptibility to diseases or pests has been noted to date.

Lasting quality: Overall bloom will last from 7–14 days depending on weather conditions.

Fragrance: Strong.

REPRODUCTIVE ORGANS

Stamens:

*Anthers.*—2–3 mm long.

*Filaments.*—Length: 5–8 mm. Color: White Group 155C with tips of Red Group 39B.

*Pollen.*—Orange Group 28A.

Pistils:

*Number.*—One; five parted.

*Length.*—10 mm.

*Stigma.*—Number: One. Color: Orange-Red Group 33A.

*Style.*—Length: 3–4 mm. Color: Green Group 138D and Orange-Red Group 33C.

Ovaries:

*Pubescence.*—Slightly pubescent.

*Length.*—7 mm.

*Width.*—1–2 mm.

*Color.*—Green.

Fruit: None observed.

GENERAL CHARACTERISTICS

'PACPAL' was selected as a replacement for the currrent variety of 'Pink Expectations' for its ability to withstand the climate of the southern United States. It performs euqally well in the northern climates also. 'PACPAL' has a more controlled growth habit where 'Pink Expectations' could become stretched and floppy. Rooting speed is similar to 'Pink Expectations' at 14 to 21 days. Flower color of 'PACPAL' is brighter than 'Pink Expectations'. This new variety has been indoor greenhouse and outdoor garden tested during the spring and summer of 1996, 1997, 1998 and 1999 where it has been exposed to a wide array of weather conditions and has performed nicely.

I claim:

1. A new and distinct variety of geranium plant substantially as shown and described.

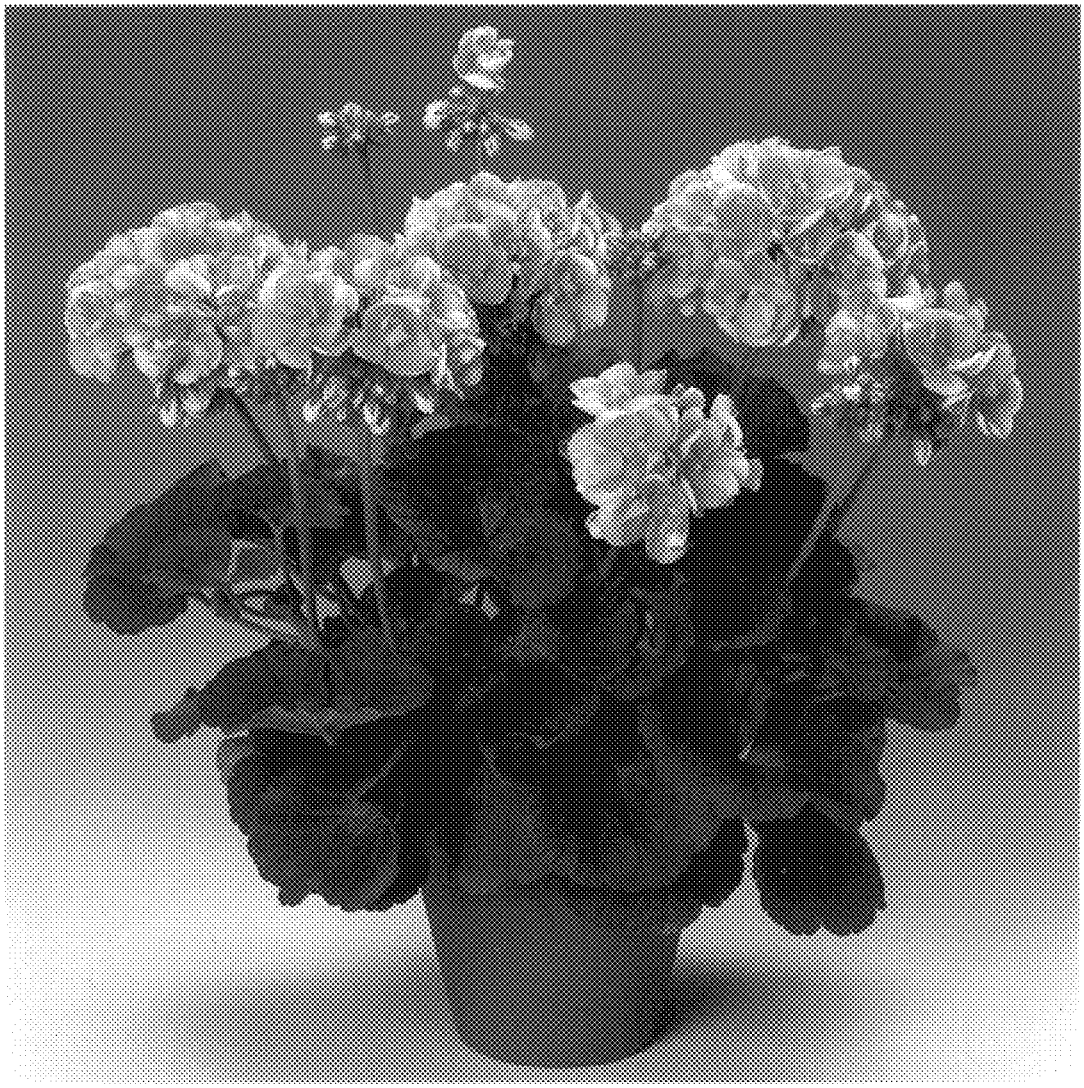

* * * * *